United States Patent

Leistner et al.

[11] Patent Number: 5,306,721
[45] Date of Patent: Apr. 26, 1994

[54] 3-(MERCAPTOALKYL)QUINAZOLINE

[75] Inventors: Siegfried Leistner; Michael Gütschow; Karl Drössler, all of Leipzig; Helmut Vieweg, Rheinfelden; Günther Wagner, Leipzig; Thomas Strohscheidt, Leipzig; Dieter Lohmann, Radebeul; Gunter Laban, Dresden; Herwart Ambrosius, Leipzig; Angela Siegling, Weissbach, all of Fed. Rep. of Germany

[73] Assignee: Arzneimittelerk Dresden G.m.b.H., Radebeul, Fed. Rep. of Germany

[21] Appl. No.: 101,269

[22] Filed: Aug. 2, 1993

Related U.S. Application Data

[63] Continuation of Ser. No. 935,124, Aug. 21, 1992, abandoned, which is a continuation of Ser. No. 689,999, Apr. 23, 1991, abandoned.

[30] Foreign Application Priority Data

| Apr. 24, 1990 | [DE] | Fed. Rep. of Germany | 340025 |
| Apr. 24, 1990 | [DE] | Fed. Rep. of Germany | 340026 |
| Apr. 24, 1990 | [DE] | Fed. Rep. of Germany | 340027 |
| Apr. 24, 1990 | [DE] | Fed. Rep. of Germany | 340029 |
| Apr. 24, 1990 | [DE] | Fed. Rep. of Germany | 340032 |

[51] Int. Cl.⁵ .............. A61K 31/505; C07D 239/96
[52] U.S. Cl. .................. 514/259; 514/260; 514/267; 544/250; 544/285
[58] Field of Search .............. 544/285, 250; 514/259, 514/267

[56] References Cited

U.S. PATENT DOCUMENTS

| 3,544,575 | 12/1970 | Scheuerer et al. | 544/285 |
| 4,684,654 | 8/1987 | Wright, Jr. et al. | 514/259 |
| 4,710,502 | 12/1987 | Wright, Jr. et al. | 514/259 |
| 4,753,944 | 6/1988 | Wright, Jr. et al. | 514/259 |

*Primary Examiner*—Mukund J. Shah
*Assistant Examiner*—Matthew V. Grumbling
*Attorney, Agent, or Firm*—Schweitzer, Cornman & Gross

[57] ABSTRACT

A compound or its tautomer of Formula I,

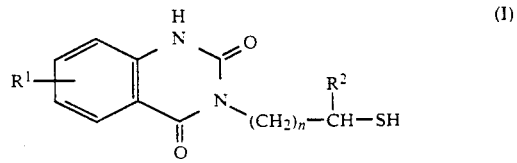

wherein
$R^1$ is hydrogen, a 6-methyl, 6-fluoro, 6-chloro, 6-bromo, or 6,7-dimethoxy residue,
$R^2$ is hydrogen, or a methyl residue,
and n is 1 or 2,
and tautomers and their pharmaceutically acceptable alkali, or ammonium salts.

5 Claims, No Drawings

3-(MERCAPTOALKYL)QUINAZOLINE

This is a continuing application of U.S. Ser. No. 935,124, filed on Aug. 21, 1992, which was a continuing application of U.S. Ser. No. 689,999, filed on Apr. 23, 1991, both now abandoned.

FIELD OF THE INVENTION

The present invention relates to 3-(mercaptoalkyl)-quinazoline-2,4(1H,3H)-diones, methods for their preparation, and to pharmaceutical compositions and processes, particularly for the treatment of diseases of the immune system, and of virus infections in living host organisms.

BACKGROUND OF THE INVENTION

There are drugs known which contain a low molecular weight active ingredient capable of creating an immunostimulating and/or immunorestorative effect. Most often levamisole hydrochloride and inosine benzoate are used at this time for such purposes.

Other active ingredients, such as NPT 15 392, i.e. erythro-9-(2-hydroxy-3-nonyl)hypoxanthine, also azimexone and ditiocarb are known to have immunomodulating, such as immunostimulating and immunorestorative effect. However, no medicinal drugs have yet been introduced, containing these active ingredients.

A standardization of known and new active ingredients, which stimulate and/or restore the immune system, is not readily possible at this time. This is due to the complexity of the immune system with its various regulatory and counterregulatory mechanisms and also to the absence of internationally agreed upon conditions for testing such agents in laboratory animals, and for clinical investigations of such agents in man. Furthermore, the aforementioned active ingredients are not available for marketing because they continue to be investigated to a greater extent with respect to their immunomodulating, immunostimulating and/or immunorestorative activity.

The difference in effect of the active ingredients on the various immunocompetent cells that react to, or are responsible for, an immune reaction also create a barrier towards a comprehensive comparability of compounds with immunostimulating and/or immunorestorative effect. These differences in effect do not permit uniform control of specific and nonspecific defense mechanisms. For example, levamisole hydrochloride has a predominantly immunorestorative effect in immunosuppressed organisms. Predominantly the T cells are stimulated, but with only a slight effect on the humoral response. Activation of nonspecific defence mechanisms is brought about by the stimulation of the hemocytophages, and the proliferation and bactericidal effect of macrophages. On the other hand, inosine benzoate manifests primarily an immunostimulating effect, among others, by an increase in the humoral immune response. The proliferation and differentiation of the T lymphocytes are also increased. The function of the macrophages is also increased through lymphokine induction.

Despite the progress in developing substances with immunomodulating, immunostimulating and/or immunorestoring activity, difficulties have been encountered in the few known methods in preparing such drugs. For example, the optical isomer of levamisole hydrochloride can be obtained by separating the diastereoisomer of the racemic tetramisole hydrochloride. The compound has a bitter, metallic taste, and after oral administration to man can result in vomiting, nausea, leucopenia, and agranulocytosis. Moreover, the physiological effect of levamisole hydrochloride is remarkably dependent on genetic factors, and the age and sex of the patient.

Inosine benzoate, which must be administered in relatively higher doses, such as about 50 mg/kg/day, can produce lead to vomiting, hyperuricemia and an increase in hematocrits. In the case of azimexone, headaches, vomiting and a decrease in haemoglobin (Hb) and erythrocytes are observed as side effects.

Therefore there is a need for drugs for the treatment of diseases of the immune system and/or for the treatment of virus infections in man and animals, as well as for methods for their preparation. There is a particular need for new drugs with immunomodulating, such as immunostimulating and/or immunorestorative action for man and animals, having improved specific and nonspecific defensive protective activity.

SUMMARY OF THE INVENTION

In accordance with the present invention, the new chemical substances with immunostimulating and/or immunorestorative and/or antiviral effects are the 3-(mercaptoalkyl)-quinazoline-2,4(1H,3H)-diones of Formula I or their tautomers,

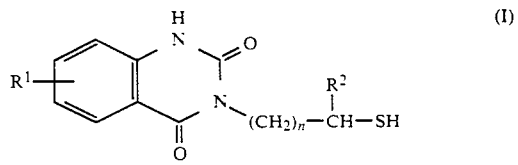

wherein
$R^1$, is hydrogen, or a 6-methyl, 6-fluoro, 6-chloro, 6-bromo, or 6,7-dimethoxy residue;
$R^2$ is hydrogen, or a methyl residue; and
n is 1 or 2, and their pharmaceutically acceptable alkali or ammonium salts.

When $R^1$ in Formula I is hydrogen, the compound of Formula II

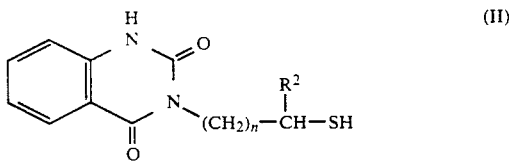

represents a special embodiment of the invention, in which $R^2$ and n have the same meanings as given above.

Suitable compounds of Formula I include:
3-(2-mercapto-ethyl)-quinazoline-2,4(1H,3H)-dione,
3-(2-mercapto-propyl)-quinazoline-2,4(1H)-dione,
3-(3-mercapto-propyl)quinazoline-2,4(1H,3H)-dione,
3-(3-mercapto-prop-1-yl)-6,7-dimethoxy-quinazoline-2,4(1H,3H)-dione,
6-chloro-3-(2-mercapto-ethyl)-quinazoline-2,4(1H,3H)-dione,
6-chloro-3-(3-mercapto-propyl)-quinazoline-2,4(1H,3H)-dione,
6-bromo-3-(2-mercapto-ethyl)-quinazoline-2,4(1H,3H)-dione, 6-bromo-3(3-mercapto-propyl)-quinazoline-2,4(1H,3H)-dione, 6-fluoro-3-(2-mercapto-ethyl)-quinazoline-2,4(1H,3H)-dione, 6-fluoro-3-(2-mercapto-propyl)-quinazoline-2,4(1H,3H)-dione, 6-methyl-3-(2-mercapto-ethyl)-quinazoline-2,4(1H,3H)-dione, 6-methyl-3-(3-mercapto-propyl)-quinazoline-2,4(1H,3H)-dione, and 6-7-dimethoxy-3-((2-mercapto-propyl)-quinazoline-2,4(1H,3H)-dione.

Pursuant to a further aspect of the present invention, the compounds of Formula I and their tautomers can be prepared either by (A) reacting a 2H-3,1-benzoxazine-2,4(1H)-dione of Formula III,

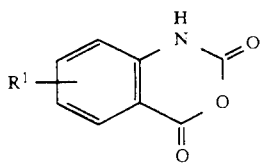

wherein $R^1$ has the same meaning as given above, with an aminoalkanol of Formula IV,

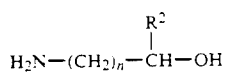

wherein $R^2$ and n have the same meanings as given above, in an aqueous reaction medium to form a compound of Formula V,

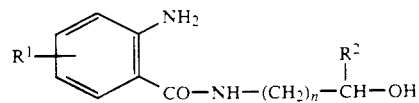

wherein $R^1$, $R^2$ and n have the same meanings as given above, and then adding a reactive solution of a $C_{1-3}$ alkanol, carbon disulfide, and potassium or sodium hydroxide, or sodium or potassium methyl xanthogenate, heating the reaction mixture suitably until reflux, then cooling and acidifying it to obtain a compound of Formula (VI)

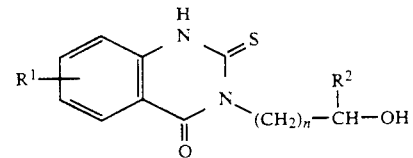

wherein $R^1$, $R^2$ and n have the same meanings as given above, then heating the compound of Formula (VI) first with a concentrated mineral acid such as hydrochloric acid, or sulfuric acid, or mixtures of mineral acids with glacial acetic acid and/or formic acid and then converting the resulting reaction mixture suitably by the subsequent addition of water, and renewed heating under reflux, to form the compound of Formula I, or a tautomer thereof; or by (B) heating a 4H-3,1-benzothiazine-2,4(1H)-dithione of Formula VII,

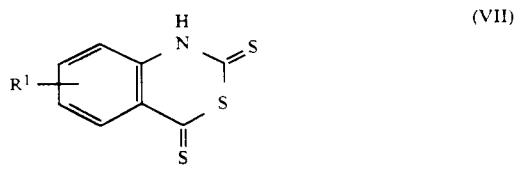

wherein $R^1$ has the same meaning as given above, with an aminoalkanol of Formula IV, in a polar organic solvent, to obtain the compound Formula VIII

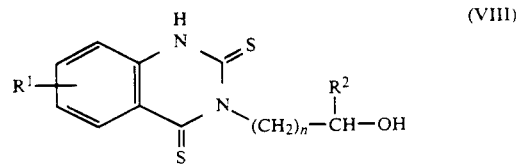

wherein $R^1$, $R^2$ and n have the same meanings as given above, reacting the compounds of Formula VIII at room temperature in an aqueous alkanolic reaction medium in the presence of an acid acceptor such as an alkali hydroxide or triethylamine, with an alkyl halide of Formula IX,

wherein $R^3$ is a $C_{1-3}$ alkyl residue, and X is an iodine or bromine ion to obtain a compound of Formula X,

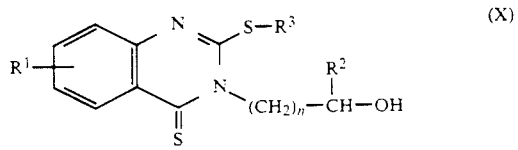

wherein $R^1$, $R^2$, $R^3$ and n have the same meanings as given above, then converting the compound of Formula X with an alkanolic mineral acid, such as absolute ethanolic hydrochloric acid, into a tricyclic quinazolinium salt of Formula XI,

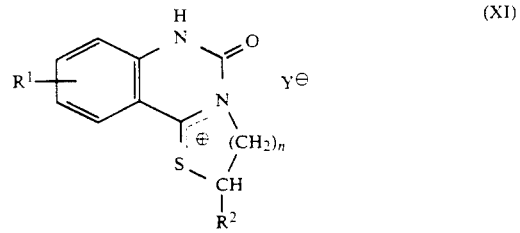

wherein $R^1$, $R^2$ and n have the same meanings as given above, and Y is an acid anion, suitably chlorine, and converting the compound of Formula XI by treatment with an aqueous alkanolic sodium hydroxide solution, followed by filtration and acidification of the filtrate with dilute mineral acid, into a compound of Formula I or a tautomer thereof; or by (C) reacting in a solution a 2H-3,1-benzoxazine-2,4(1H)-dione of Formula III, with a solution of a bis-(aminoalkyl)-disulfan of Formula XII

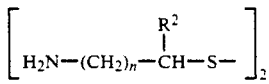

or a salt thereof, suitably a dihydrochloride, wherein $R_2$ and n have the same meanings as given above, to obtain a compound of Formula XIII

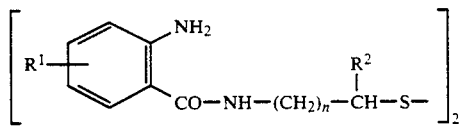

wherein $R^1$, $R^2$ and n have the same meanings as given above. Then reacting in a solvent or a mixture of solvents the compound of Formula XIII with an alkyl chloroformate of Formula XIV,

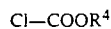

wherein $R^4$ is a $C_{1-3}$ alkyl residue, to obtain a compound of Formula XV

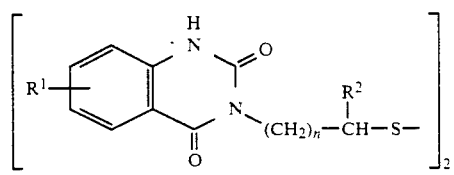

wherein $R^1$, $R^2$ and n have the same meanings as given above, and optionally after purification or drying, converting the compound of Formula XV, in a solvent or solvent mixture with nascent hydrogen into a compound of Formula I, or a tautomer thereof; or by (D) reacting a 3-(haloalkyl)-2,4-dioxo-1,2,3,4-tetrahydroquinazoline of Formula XVI,

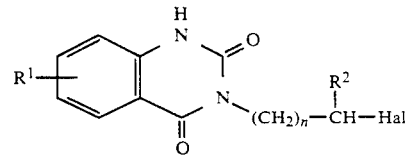

wherein $R^1$, $R^2$ and n have the same meanings as given above, and Hal is a chlorine or bromine ion, with thiourea at a temperature of from about 80° C. to about 150° C. to form an S-[-(2,4-dioxo-1,2,3,4-tetrahydroquinazoline-3-yl)-alkyl]-isothiuronium halide of Formula XVII,

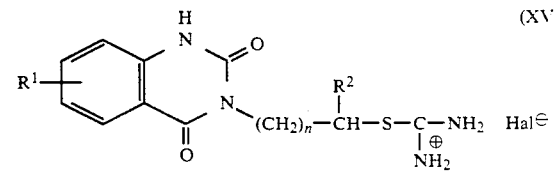

wherein $R^1$, $R^2$, n, and Hal have the same meanings as given above and, after optionally isolating said isothiuronium halide, converting it by an alkali hydroxide solution, optionally in the presence of nitrogen as an inert gas, at temperatures of from about −10° C. to about +15° C. to a compound of Formula I, or a tautomer thereof.

The sequences and parameters of the method variants described under (A) to (D) above, can be varied within wide limits. For example, in the method variant (A), the mixture of solids resulting from the reaction of the compound of Formula VI with a concentrated mineral acid, such as hydrochloric acid or sulfuric acid or a mixture of such mineral acids with glacial acetic and/or formic acid, can be isolated and subsequently, by being heated in dilute mineral acid, converted into a compound of Formula I or a tautomer thereof.

In the method variant (D) further embodiments of the invention, can include:

reacting a compound of Formula XVI with thiourea in the molar ratio of from about 1:1 to about 1:3;

in preparing a compound of Formula XVII, the reaction is suitably carried out under reflux, in a protic solvent, suitably in methyl glycol, or 1-butanol;

reacting a compound of Formula XVI suitably under vacuum, particularly if the compound is not very reactive;

reacting of a compound of Formula XVII form a compound of Formula I in an aqueous, or an aqueous/ethanolic alkali hydroxide solution, suitably in a sodium hydroxide solution of from about 0.1 to about 1.0 moles/l, suitably about 0.25 moles/l concentration, under optional stirring; and/or reacting a compound of Formula XVII to form a compound Formula I under an inert nitrogen atmosphere, which precaution can also be advantageous in the recrystallization of the compound of Formula I.

In a further embodiment of the process variant (D) of the present invention, the reaction of a compound of Formula XVI to a compound of Formula I can also be conducted by omitting the separation of a compound of Formula XVII, while otherwise retaining and analogously using the aforementioned reaction conditions.

According to a further embodiment of any of the aforementioned process variants (A)-(D) of the invention, the compounds of Formula I can be converted in a known manner into their alkali or ammonium salts in a manner known per se.

The present invention further includes pharmaceutical compositions for the treatment of immune diseases and/or virus infections in man and in animals. These pharmaceutical compositions contain as an at least one active ingredient one or more compounds of Formula I, wherein $R^1$, $R^2$ and n have the same meanings as given above, or their tautomers, or their pharmaceutically acceptable alkali, or ammonium salts.

Due to the immunoregulatory, immunostimulatory and immunorestorative properties of compounds of Formula I, those pharmaceutical compositions containing these compounds, are particularly suitable for the treatment of diseases of the immune system in living hosts. Further, due to the antiviral characteristics of compounds of Formula I, those same pharmaceutical compositions are also suitable for the treatment of viral diseases in host organisms.

A suitable embodiment of the compositions of the present invention contain as an active ingredient a compound of Formula II, wherein $R^2$ and n have the same meanings as given above, their tautomers, or their pharmaceutically acceptable alkali, or ammonium salts. A particularly suitable pharmaceutical compositions in accordance with the present invention contains as active ingredient 3-(2-mercaptoethyl)-quinazoline-2,4(1H,3H)-dione, or a tautomer, or a pharmaceutically acceptable alkali, or ammonium salts thereof.

Cherbuliez et al. (Helv. chim. Acta, Vol. 50, 1967, pp. 1440–1452) converted three compounds of Formula VI, in two steps into 2-(o-carboxyphenylamino)-4,5-dihydrothiazothiazole and −5,6-dihydro-4H-1,3-thiazine respectively, and analyzed its structure by elementary analysis, $^1$H-NMR, U.V., and I.R.

As far as the pharmacological properties of the compounds of Formula I are concerned, they or particularly suitable for the treatment of diseases of the immune system and/or of virus infections in man and in animals. The immunoregulatory, immunostimulatory, immunorestorative, and antiviral properties of these compounds were investigated in some detail.

The examination of immunoregulatory effectiveness of compounds of Formula I was carried out on the guinea pig (albino colony breed), by employing a percutaneous test to demonstrate delayed contact hypersensitivity (effector T lymphocyte activity), and Takátsy test to demonstrate DNP-specific serum antibodies (humoral immune response).

The testing of immunostimulatory effects was also conducted on the mouse (inbred CBA strain) by detection through the plaque test for detecting SE (sheep erythrocyte) -specific immunoglobulin M (IgM) and immunoglobulin G (IgG) PFC (plaque forming cells), and by the rosette test.

The detection of immunorestorative effects after injury to the immune system was carried out also by the plaque test for detecting SE-specific IgM, and IgG PFC, and by the rosette test.

Examination of antiviral efficacy was conducted in vitro chicken embryo cells with different virus groups.

1. Investigation of immunoregulatory efficacy 1.1 Percutaneous test for detecting contact hypersensitivity The epicutaneous application of dinitrofluorobenzene (DNFB) led to the development of a delayed hypersensitivity in guinea pigs and mice, an immune status, which is linked to the clonal reproduction of antitrinitrophenyl (TNP)-specific T lymphocytes ($T_{DTH}$-ly). If, after a latency period of at least 5 days, there is a renewed application of DNFB, lymphokines are released through the reaction with the $T_{DTH}$-ly of this region of the skin and thus lead to a locally limited inflammatory reaction.

Seven days after the immunization with 1% DNFB, the sides of the experimental animals were depilated and tested by the application of one drop each of the 0.5%, 0.1%, 0.05, 0.025% and 0.01% DNFB solution. The concentration that still demonstrates a positive result, is inversely proportional to the degree of the sensitization. The test results are obtained from the severity and number of the positive skin reactions, and the stimulation index (SI) is obtained from the comparison of test animals and control animals.

The test substance is orally administered. A daily dose of 2 mg/kg of body weight, as an aqueous suspension, was administered daily by a stomach tube. Duration of treatment: 1 day + 1 (one day after the immunization), up to +6. The control animals received only the lactose content of the composition.

1.2 Takátsy test

After immunization with DNFB, dinitrophenyl (DNP)-specific humoral antibodies, which preferentially belong to the $IgG_1$ substance class, are developed in guinea pigs. Blood was taken from the experimental animals by puncture of the heart fourteen days after the primary epicutaneous application of DNFB. The antibody (AB) concentration was determined according to the method described by G. Takátsy: A New Method for the Preparation of Serial Dilutions in a Quick and Accurate Way, (Kisérletes Orvostudomány, Hungary, Vol. 2, 1950, pp. 263–396). TNP-laden sheep erythrocytes were used as indicator cells coupled according to Rittenberg and Pratt (M. B. Rittenberg, and K. L. Pratt, Antitrinitrophenyl Plaque Assay. Primary Response of BALB/c Mice to Soluble and Particulate Immunogen, Proc. Soc. Exp. Biol. Med., Vol. 132, 1969, pp. 575–579).

The degree of sensitization in percent and the concentration of serum antibodies expressed as antibody titer difference is compared below to the respective control group (screening values).

| Compound of Example No. | Contact Dermititis (Control: 100) | | DNP-Specific Antibodies |
|---|---|---|---|
| | 24-Hour Reaction | 48-Hour Reaction | |
| 6 | 70 | 40 | −1.5 |
| 7 | 230 | | +1.8 |
| 12 | 120 | 130 | +0.3 |
| 13 | 120 | 130 | ±0 |
| 8 | 100 | 115 | ±0 |
| 5 | 150 | 120 | −0.6 |
| 3 | 100 | | +1.0 |
| 2 | 180 | | ±0 |
| 14a | 60 | 60 | −1.9 |
| 14b | 105 | 100 | +2.2 |
| 14c | 90 | 105 | ±0 |
| 14d | 100 | 150 | ±0 |
| 14e | 100 | | ±0 |

The results demonstrate that the compounds of Formula I have a readily detectable effect on the effector-T-lymphocyte-dependent delayed hypersensitivity. A contact dermatitis value of 120 or more, i.e. corresponding to an at least 20% increase compared to the control, or of less than 80 are taken as proof of a stimulatory or suppressor effect, respectively. Antibody values of $> +1$ or $< -1$ illustrate the stimulatory or suppressor effect, respectively, of the substances on the humoral response.

2. Investigations of Immunostimulatory Action 2.1 Plaque Test for the Detection of SE-Specific IgM and IgG Plaque Forming Cells (PFC)

To check the immunostimulatory effects, the humoral immune response effect of compounds of Formula I was also investigated in mice of the inbred CBA strain and determined by means of the haemolysis plaque test (HPT). This technique permits the PFC, which produce IgM and IgG antibodies, to be determined quantitatively and separately. The immunization with sheep erythrocytes (SE) was carried out on day 0, the substance was administered orally in a daily dose of $1 \times 10^{-5}$ moles/kg of body weight; on days $-1$ to $+3$ relative to the determination of the IgM PFC, or on days +1 to +5 relative to the determination of the IgG PFC.

By means of the daily administration, extending over 5 days, of 2.0 mg of the compound of Example 1 per kg of body weight, it was possible to increase the number of IgM PFC to an average value of 352% of the 100% value of the control group. The same form of treatment led to an increase in the IgG PFC to 497% relative to the 100% control. In both cases, the difference between the experimental value and the control value proved to be significant in the t-test with $p<0.001$. It becomes clear that a daily treatment extending over 5 days with the compound of Example 1, produces a highly significant increase in the SE-specific IgM and IgG PFC in the CBA mouse.

2.2 Rosette Test (SE-specific rosettes)

According to Burnet's Theory, lymphocytes carry immunoglobulin receptors on their surface. These receptors are directed against a particular antigen and are detectable by a reaction with the specific antigen. The determination of the number of rosette-forming cells (RFC) can serve as a measure of the strength of an incipient immune reaction and consequently also reproduce the effects of a suppression or stimulation of cell-proliferative processes.

Three days after the intravenous immunization with $2 \times 10^5$ SE in 0.2 ml physiological salt solution, the experimental animals were killed by hyperdistention, the spleen was removed and, after addition of Parker medium at pH 7.4, rubbed through Müller gauze. The work to recover the cell suspension was carried out in an ice-cooled water bath from about 0° C. to about 4° C. The determination of the cell density was carried out in a Neubauer counting chamber. Next, the cell count was adjusted to $1 \times 10^7$ nuclei-containing cell (NCC) per ml of medium, a count that was kept constant for all experimental formulations. Of this spleen cell suspension ($1 \times 10^7$ NCC/ml), 0.9 ml were then mixed with 0.1 ml of a 5% washed SE suspension and incubated for 24 hours at 4° C. An NCC, which was surrounded by at least 4 erythrocytes and was identifiable, was rated as a rosette.

A significant production of SE-specific rosette-forming cells were noted after oral administration of compounds of Examples 2, 6 and 14e.

3. Determination of the Immunorestorative Efficacy

The determination of the immunorestorative activity of compounds of Formula I was conducted by first damaging the immune system of the experimental animals (CBA inbred mice) by chemotherapy with cyclophosphamide, carrageenan, iloprost, or by radiation. The test was carried the plaque test for detecting SE-specific IgM and IgG PFC, and the rosette test.

The examination of the immunorestorative effects of compounds of Example 1 was carried out by damaging the immune system of the experimental animals by cyclophosphamide (CY), and subsequent testing by sheep erythrocycle SE-specific plaque forming cells PFC.

The immune system of the animals was damaged by the injection of 150 mg/kg of body weight on day −1 before the immunization for both the test and the control groups. Immunization was carried out by the intraperitoneal injection of $4 \times 10^8$ SE in 0.2 ml of phosphate buffered saline (PBS) solution.

Each of the experimental animals of the test group received by oral administration 2 mg of the compound of Example 1 per kg of body weight on the days −2, −1, 0, +1 and +2. The SE-specific IgM and IgG PFC was detected by the plaque test.

The following table summarizes the IgM PFC results.

| | IgM PFC/$10^6$ | |
|---|---|---|
| Day of testing | Control Only CY. compound of Example 1 | Test CY + compound of Example 1 |
| +3 | 37.5 ± 27.1 | 31.7 ± 26.6 |
| +4 | 49.7 ± 32.9 | 59.8 ± 26.6 |
| +5 | 56.8 ± 27.6 | 125.2 ± 32.7 |
| +6 | 74.7 ± 73.4 | 47.8 ± 32.7 |

Under the influence of the compound of Example 1, there is a measurable recovery of the immunological reactivity, which is significant on the 5th day with $p<0.05$.

The following table summarizes the IgG PFC results.

| | IgG PFC/$10^6$ spleen cells | |
|---|---|---|
| Day of Testing | Control Only CY, without compound of Example 1 | Test CY + compound of Example 1 |
| +6 | 26.7 ± 12.1 | 88.3 ± 24.8 |
| +7 | 46.7 ± 16.3 | 128.3 ± 28.6 |
| +8 | 63.3 ± 24.2 | 58.3 ± 43.6 |

The compound of Example 1 significantly increases the number of IgG PFC in CY-suppressed experimental animals on the 6th and 7th days ($p<0.05$ and $p<0.01$, respectively).

4. Determination of Antiviral Effecacy

The antiviral effects in a living host were determined in a number of test series after the test substance was dissolved in dimethyl sulfoxide (50 mmoles/l) and the resulting stock solution was subsequently diluted 1:200 to 1:1,600 with conventional physiological media. By this procedure it was possible to avoid a nonspecific effect of the organic solvent.

The antiviral testing was carried out in vitro with smallpox, influenza, herpes simplex, and rhabdoviruses, all with chicken embryocells, human fibroblasts/rhabdoviruses, and coxsackie viruses, with (MDBK) bovine kidney cells, and smallpox and herpes simplex viruses, and adenoviruses with human kidney (RH) cells, in accordance with:

- grading replication experiments according to Tonew and Tonew (Arch. Ges. Virusforsch. Vol. 33, 1971, pp. 319–329
- plaque reduction tests according to Tonew and Tonew (Zbl. Bakter. Hyg. I. Orig., Vol. 211, 1969, pp. 437–444 (1969), and
- the Dynatech microtiter system of Tonew and Glëck (J. Basic Microbiol. 3, 1986, 173).

Determination of cell compatibility of the substance was carried out with the same cells (see the following test series 1, 2, 3, 4 and 5). As shown by the test series 1 to 5, the tested compounds of Formula I are tolerated by cells in therapeutic concentrations and exceptionally strongly inhibit a variety of human and animal viruses.

The abbreviation "n.s." means that the result is not significant.

Test Series 1

Determinations of cell compatibility of 3-(2-mercapto-ethyl)-quinazoline-2,4(1H,3H)dione were carried out by using 2 day old primary chicken embryo cells. RH human kidney cells—permanent cell line (RH), and bovine kidney cells—permanent cell line (MDBK), and 2 day old human fibroblasts.

| Cells | Concentration of the substance in μmoles/l in the maintenance medium | | | | |
|---|---|---|---|---|---|
| | 1,000 | 500 | 250 | 125 | 62.5 |
| HEZ* | +++ | + | ∅ | ∅ | ∅ |
| RH | +++ | ++ | ∅ | ∅ | ∅ |
| MDBK | ++++ | ++ | ∅ | ∅ | ∅ |
| HFi | ++ | ∅ | ∅ | ∅ | ∅ |

Key to table:
*HEZ means chicken embryo cells
∅ means no morphological changes in the cells on the 5th day of the reading by microscope.
++++ means complete change in the cell layer in the form of rounding off, granulation and detachment of the cells from the glass wall.
+++ means similar change in ¾ of the cells.
++ means similar changes in ½ of the cells.
+ means similar changes in ¼ of the cells.

Test Series 2

The antiviral activity of 3-(2-mercapto-ethyl)-quinazoline2,4(1H,3H)-dione was examined on chicken embryo cells in the grading replication cycle

| Virus strain | Concentration in μmoles/l | Lowering the virus yield in comparison to the unknown control in $\log_{10} TCID_{50}/0.2$ ml | % Inhibition |
|---|---|---|---|
| Vaccinia | 250 | 5.67 | >99.99 |
| Lister | 125 | 4.0 | 99.99 |
| | 62.5 | 2.5 | 99.68 |
| | 31.25 | 1.0 | 99.0 |
| Influenza | 250 | 6.23 | >99.99 |
| A/WSN | 125 | 4.67 | >99.99 |
| | 62.5 | 4.25 | >99.99 |
| | 31.25 | 2.5 | 99.50 |
| Herpes simplex type 1 | 250 | 1.0 | 99 |
| Vesicular | 125 | 0.33 | n.s. |
| Stomatitis | 250 | 3.0 | 99.9 |
| Indiana | 125 | 0.5 | n.s. |

Each result is the average of three experiments. The substance did not have antiviral activity against the coxsackie A 9 virus and the adenovirus type 4.

The therapeutic index is the ratio of the maximum tolerated dose to the minimum effective dose. The therapeutic indices for the vaccinia virus, were both 8.

Test Series 3

The antiviral action of 3-(2-mercapto-ethyl)-quinazoline-2,4(1H,3H)-dione was examined on the RH cell line in the grading replication cycle.

| Virus strain | Concentration in μmoles/l | Lowering the virus yield in comparison to the unknown control in $\log_{10} TCID_{50}/0.2$ ml | % Inhibition |
|---|---|---|---|
| Vaccinia | 250 | >4.0 | >99.99 |
| Lister | 125 | >4.0 | >99.99 |
| | 62.5 | 4.0 | 99.99 |
| | 31.25 | 3.5 | >99.99 |
| Herpes simplex type 1 Kupka | 250 | 6.0 | >99.99 |
| | 125 | 5.5 | >99.99 |
| | 62.5 | 0.75 | n.s. |

The result is the average of two experiments

Test Series 3

The antiviral action of 3-(2-mercapto-ethyl)-quinazoline-2,4(1H,3H)-dione was examined on the RH cell line in the grading replication cycle

| Virus strain | Concentration in μmoles/l | Lowering the virus yield in comparison to the unknown control in $\log_{10} TCID_{50}/0.2$ ml | % Inhibition |
|---|---|---|---|
| Vaccinia | 250 | >4.0 | >99.99 |
| Lister | 125 | >4.0 | >99.99 |
| | 62.5 | 4.0 | 99.99 |
| | 31.25 | 3.5 | >99.99 |
| Herpes simplex type 1 Kupka | 250 | 6.0 | >99.99 |
| | 125 | 5.5 | >99.99 |
| | 62.5 | 0.75 | n.s. |

The result is the average of two experiments

Test Series 4

The antiviral action of 3-(2-mercapto-ethyl)-quinazoline-2,4(1H,3H)-dione was examined in the plaque reduction test

| Virus strain | Concentration in μmoles/l | Plaque reduction in % of the virus control on primary chicken embryo cells |
|---|---|---|
| Vaccinia | 250 | 100 |
| Lister | 125 | 96 |
| | 62.5 | 92 |
| | 31.25 | 87 |
| influenza | 250 | 100 |
| A/WSN | 125 | 98 |
| | 62.5 | 92 |
| | 31.25 | 85 |
| vesicular stomatitis Indiana | 250 | 45 n.s. |
| | 125 | 15 |
| | 62.5 | 0 |

The result is the average of two measurements

Test Series 5a

The antiviral action of 3-(3-mercapto-prop-1-yl)-6,7-dimethoxy-quinazoline-2,4(1H,3H)-dione was examined on RH cell line in the grading replication cycle

| Virus strain | Concentration in μmoles/l | Lowering the virus yield in comparison to the unknown control in $\log_{10} TCID_{50}/0.2$ ml | % Inhibition |
|---|---|---|---|
| Vaccinia | 250 | 5.0 | >99.99 |
| Lister | 125 | 5.0 | >99.99 |
| | 62.5 | 5.0 | >99.99 |
| | 31.25 | 2.84 | 99.84 |
| Herpes simplex type 1 | 250 | 6.5 | >99.99 |
| | 125 | 6.5 | >99.99 |
| | 62.5 | 5.0 | >99.99 |
| | 31.25 | 3.67 | 99.97 |
| Influenza A/WSN | 250 | 6.17 | 99.99 |
| | 125 | 2.0 | 99.0 |

-continued

| Virus strain | Concentration in μmoles/l | Lowering the virus yield in comparison to the unknown control in log$_{10}$ TCID$_{50}$/0.2 ml | % Inhibition |
|---|---|---|---|
| | 62.5 | 0.5 | n.s. |
| | 31.25 | 0 | |

Test Series 5b

The antiviral action of 3-(3-mercapto-prop-1-yl)-6,7-dimethoxy-quinazoline-2,4(1H,3H)-dione was examined on chicken embryo fibroblasts in the grading replication cycle

| Virus strain | Concentration in μmoles/l | Lowering the virus yield in comparison to the unknown control in log$_{10}$ TCID$_{50}$/0.2 ml | % Inhibition |
|---|---|---|---|
| Vaccinia | 250 | 5.0 | >99.99 |
| Lister | 125 | 5.0 | >99.99 |
| | 62.5 | 3.5 | 99.93 |
| | 31.25 | 3.0 | 99.9 |
| Influenza | 250 | 5.0 | >99.99 |
| A/WSN | 125 | 5.0 | >99.99 |
| | 62.5 | 2.0 | 99.0 |

The invention is described in greater detail by reference to the following illustrative examples.

EXAMPLE 1

Preparation of 3-(2-mercapto-ethyl)-quinazoline-2,4(1H,3H)-dione

This is a compound of Formula I wherein $R^1$ and $R^2$ are both hydrogen, and n is 1.

(a) 2.4 g (10 mmoles) of 3-(2-hydroxyethyl)-quinazoline-2,4(1H,3H)-dithione of Formula VIII, wherein $R^1$ and $R^2$ are H, n is 1, is dissolved in a methanolic sodium hydroxide solution of 20 ml 0.5N NaOH, and 7 ml CH$_3$OH, treated with 1.6 g of methyl iodide of Formula IX, and is intensively shaken in a closed vessel at room temperature. The resulting precipitate is removed and washed with a small amount of 50% methanol and dried. Yellow crystals of the intermediate 3-(2-hydroxy-ethyl)-2-methylthio-quinazoline-4(3H)-thione of Formula X, wherein $R^1$ and $R^2$ are both H, $R^3$ is CH$_3$, n is 1, having an elemental analysis of C$_{11}$H$_{12}$N$_2$OS$_2$ (252.4) are recovered, with a melting point (M.P.) of 117° C.–118° C. (CH$_3$OH), and a yield of 92%.

(b) The TLC-pure compound (505 mg), produced in Example 1(a), is dissolved in 9 ml methanolic hydrochloric acid containing 30 g HCl gas/200 ml of absolute methanol, and kept in a closed vessel, at first for 24 hours at room temperature and then for a further 24 hours at −20° C. The precipitate formed is washed with absolute diethyl ether and dried in a vacuum desiccator over KOH/H$_2$SO$_4$. 340 mg yellow crystals of the intermediate 2,3-dihydro-5-6H-oxo-thiazolo/3,2-c/quinazoline-4-ium chloride hydrate of Formula XII is obtained wherein $R^1$ and $R^2$ are both hydrogen, n is 1, and y is Cl, having an elemental analysis of C$_{10}$H$_9$ClN$_2$OS.H$_2$O (258.7), IR: CO bands at 1740 cm$^{-1}$, and MS: m/e 204 (molecule ion peak of the basic base).

(c) 700 mg of the compound obtained in Example 1(b), is dissolved with stirring in ethanolic sodium hydroxide solution of 5 ml 3N NaOH, 35 ml water, and 20 ml ethanol. After about 15 minutes, the reaction solution is filtered and dilute hydrochloric acid is added with stirring to the colorless filtrate until no further precipitate is formed. The recovered precipitate is washed thoroughly with water and dried in a vacuum desiccator over concentrated H$_2$SO$_4$. 610 mg of a TLC-pure (mobile phase: toluene/acetone/methanol=7:3:1; v/v/v) end product of colorless crystals, of 3-(2-mercapto-ethyl)-quinazoline-2,4(1H.3H)-dione of Formula I, wherein $R^1$ and $R^2$ are both H, and n is 1, is obtained. It has an elemental analysis of C$_{10}$H$_{10}$N$_2$O$_2$S (222.2), and M.P.: 192° C.–193° C. (CHCl$_3$/petroleum ether).

A further portion of the end product can be recovered, contaminated with small amounts of bis[2-(2,4-dioxo-1,2,3,4-tetrahydro-quinazoline-3-yl)-ethyl]-disulfan of Formula XV, wherein $R^1$ and $R^2$ are both H, and n is 1, by concentrating to dryness the filtrate obtained after filtering off the crystalline thiazoloquinazolinium chloride hydrate, and treating the residue as described in Example 1(c).

EXAMPLE 2

Preparation of 3-(3-mercapto-prop-1-yl)-6,7-dimethoxy-quinazoline-2,4(1H,3H)-dione.

This is a compound of Formula I wherein $R^1$ is a 6,7-dimethoxy residue, $R^2$ is H, and n is 2.

(a) 12.5 g, 0.15 moles thiophosgene is added dropwise as a 10% solution in dioxane to a mixture of 19.9 g (0.1 moles) 2-amino-4,5-dimethoxy-benzoic acid, 200 ml dioxane and 32 g (0.3 moles) triethylamine, while the mixture is cooled, and stirred in an ice bath. Stirring is continued for 3 hours at room temperature. The reaction mass is then mixed with 1,000 ml water, and acidified with dilute hydrochloric acid. The resulting precipitate is recrystallized from dioxane/water to obtain the intermediate 6,7-dimethoxy-2-thioxo-3,1-benzoxaine-4(1H)-one. The elemental analysis is C$_{10}$H$_9$NO$_4$S (239.2), M.P.: 211° C.–213° C. (dioxane/water), at a yield of 75%.

(b) The 2 g of 3,1-benzoxazine derivative, obtained in Example 2(a), is dissolved in a minimal amount of hot pseudocumene, treated with 2.0 g phosphoric(V) sulfide, and is refluxed for 20 minutes. After the addition of a further 1.0 g of phosphoric(V) sulfide, refluxing is continued for a further 15 minutes. The reaction solution is filtered while still hot. After standing for 12 hours, the resulting precipitate is filtered off with suction, washed with a little methanol, and dissolved in 0.5N sodium hydroxide solution. Then the alkaline solution is filtered without delay into excess dilute hydrochloric acid and the red crystalline precipitate of the intermediate 6,7-dimethoxy-3,1,-benzothiazine-2,4(1H)-dithione of Formula VII, wherein $R^1$ is a 6,7-dimethoxy residue, is separated and washed with water. The elemental analysis is C$_{10}$H$_9$NO$_2$S$_3$ (271.4), M.P.: 247° C.–249° C. (ethyl acetate), at a yield of 60%.

(c) The 2.7 g (10 mmoles) of 3,1-benzothiazine derivative obtained in Example 2(b) is heated for 2 hours at 60° C. together with 1.2 g triethylamine, 0.82 g (11 mmoles) 3-amino-propane-1-ol of Formula IV, wherein $R^2$ is H, and n is 2, and 12 ml ethanol under reflux. The reaction mixture is acidified after cooling, with dilute hydrochloric acid and the yellow orange crystalline precipitate of the intermediate 3-(3-hydroxy-prop-1-yl)-6,7-dimethoxy-quinazoline-2,4(1H,3H)-dithione of Formula VIII, wherein $R^1$ is a 6,7-dimethoxy residue, $R^2$ is H, and n is 2, is filtered off with suction after 12 hours and washed with water. The elemental analysis is $C_{13}H_{16}N_2O_3S_2$ (312.4), M.P. 239° C. (2-propanol), at a yield of 61%.

In the following Examples 2(d)–(f) the dithione, obtained in Example 2(c) is further reacted to the final product by the method described in Example 1 (a)–(c).

(d) 3-(3-Hydroxy-prop-1-yl)-6,7-dimethoxy-2-methylthio-quinazoline-4(3H)-thione of Formula X, wherein $R^1$ is a 6,7-dimethoxy, $R^2$ is H, $R^3$ is a $CH_3$ residue, and n is 2. Yellow crystals having an elemental analysis of $C_{14}H_{18}N_2O_3S_2$ (326.4), M.P.: 168° C.–170° C., and yield of 76%.

(e) 3,4-Dihydro-9,10-dimethoxy-6-oxo-2H,7H-1,3-thiazino-/3,2-c/quinazoline-5-ium chloride of Formula XI, wherein $R^1$ is a 9,10-dimethoxy residue, $R^2$ is H, n is 2, and Y is Cl. Yellowish crystals having an elemental analysis of $C_{13}H_{15}ClN_2O_3S$ (314.8), IR: CO bands at 1720 $cm^{-1}$, M.P.: 197° C.–198° C. (after washing with diethyl ether), and yield of 74%.

(f) 3-(Mercapto-prop-1-yl)-6,7-dimethoxy-quinazoline-2,4(1H,3H)-dione of Formula I, wherein $R^1$ is a 6,7-dimethoxy residue, $R^2$ is H, and n is 2. Colorless crystals having an elemental analysis of $C_{13}H_{16}N_2O_4S$ (296.3), M.P.: 236° C. (methyl glycol), IR: SH bands at 2,540 $cm^{-1}$, and yield of 81%.

EXAMPLE 3

Preparation of
3-(2-mercapto-ethyl)-6,7-dimethoxy-quinazoline-2,4(1H,3H)-dione

This is a compound of Formula I, wherein $R^1$ is a 6,7-dimethoxy residue, $R^2$ is H, and n is 1. This compound is prepared from 6,7-dimethoxy-3,1-benzothiazine-2,4(1H)-dithione and 2-amino-1-ethanol by a method similar to that described in Examples 1 and 2.

The compound comprises colorless crystals, having an elemental analysis of $C_{12}H_{14}N_2O_4S$ (282.4), IR: SH bands at 2520 $cm^{-1}$, CO bands at 1697 and 1645 $cm^{-1}$, M.P.: 312° C.–314° C. (chloroform/petroleum ether), and yield of 84% (based on the last step of the synthesis).

The following intermediates were isolated and characterized during the preparation:

(a) 3-(2-Hydroxyethyl)-6,7-dimethoxy-quinazoline-2,4-(1H,3H)-dithione of Formula VIII, wherein $R^1$ is a 6,7-dimethoxy residue, $R^2$ is H, and n is 1. Yellow, orange crystals, having an elemental analysis of $C_{12}H_{14}N_2O_3S_2$ (298.4), M.P.: 181° C.–183° C. (dioxane/water), and yield of 92%.

(b) 3-(2-Hydroxyethyl)-6,7-dimethoxy-2-methylthio-quinazoline-4(3H)-thione of Formula X, wherein $R^1$ is a 6,7-dimethoxy residue, $R^2$ is H, $R^3$ is a $CH_3$ residue, and n is 1. Yellow crystals, having an elemental analysis of $C_{13}H_{16}N_2O_3S_2$ (312.4), M.P.: 187° C.–188° C. (2-propanol), and yield of 72%.

(c) 8,9-Dimethoxy-5-oxo-2,3-dihydro-6H-thiazolo/3,2-c/quinazoline-4-ium chloride of Formula XI, wherein $R^1$ is a 8,9-dimethoxy residue, $R^2$ is H, n is 1, and Y is Cl. Yellowish crystals having elemental analysis of $C_{12}H_{13}ClN_2O_3S$ (300.8), IR: CO bands at 1715 $cm^{-1}$, M.P.: 201° C.–205° C. (after washing with diethyl ether), and yield of 67%.

EXAMPLE 4

Preparation of
3-(2-mercapto-ethyl)-quinazoline-2,4(1H,3H)-dione

This is a compound of Formula I, wherein $R^1$ and $R^2$ are H, and n is 1.

(a) 6.5 g, (40 mmoles) 2H-3,1-benzoxazine-2,4-(1H)-dione of Formula III, wherein $R^1$ is H, was dissolved in 30 ml dimethylformamide and treated with the suspension prepared from 4.5 g (20 mmoles) of cystaminium chloride (cystamine dihydrochloride) of Formula XII. 0.2 HCl, wherein $R^2$ is H, and n is 1, 20 ml dimethylformamide, and 6 g (60 mmoles) triethylamine. The reaction mixture was heated for 45 minutes on a water bath at 70° C. The precipitate is removed after cooling, and is washed with 20 ml dimethylformamide. The filtrate and the wash solution are combined and poured into 150 ml water. After several hours in the refrigerator, the resulting precipitate is filtered off with suction, washed with water and dried. In all, 7.0 g (90% of the theoretical amount) of TLC-pure bis-[2-(2-amino-benzoylamino)-ethyl]-disulfan of Formula XIII, wherein $R^1$ and $R^2$ are H, and n is 1, are obtained, which can be used for the subsequent reaction without further purification. The M.P. is 129° C.–131° C. (ethanol/water).

(b) 0.98 g, (2.5 mmoles) bis-[2-(2-amino-benzoylamino)-ethyl]-disulfan obtained in Example 4(a) is dissolved in 10 ml pyridine and cooled in an ice bath. Then, still in the ice bath, 1 ml (10 mmoles) ethyl chloroformate of Formula XIV, wherein $R^4$ is a $C_2H_5$ residue, is added dropwise. The reaction mixture is refluxed for 1 hour. After cooling, it is added to a mixture prepared from 15 ml HCl (1 mole/l) and 10 ml ice water. After resting for a considerable time in a refrigerator, the resulting precipitate is filtered off with suction, washed with water, and dried. The resulting intermediate obtained is suspended in powdered form in a mixture of 8 ml NaOH (3 moles/l) and 1.6 ml ethanol, shaken for 6 hours in a closed reaction vessel, and rested for a further 24 hours at room temperature. 30 ml warm water is added and the reaction mass is filtered. The filtrate is acidified with dilute HCl, and the resulting precipitate of the intermediate bis-[2-(2,4-dioxo-1,2,3,4-tetrahydro-quinazoline-3-yl)-ethyl]-disulfan of Formula XV, wherein $R^1$ and $R^2$ are both H, and n is 1, is filtered off with suction, and is dried.

0.85 g of TLC-pure intermediate (77% of the theoretical yield) is obtained, which can be used for the subsequent reaction without further purification. M.P. 270° C.–272° C. (1-propanol).

(c) 200 mg of the product of Example 4(b) above 200 mg zinc dust, and 12 ml acetic acid are refluxed for 3 hours, then treated with a mixture prepared from 16 ml HCl (1 mole/l) and 28 ml water, and brought to boiling once again. After filtration, the filtrate is kept for 1 to 2 days in a closed vessel in the refrigerator. The precipitate is filtered off with suction and dried. The yield is 150 mg (75% of the theoretical yield) of TLC-pure and product of 3-(2-mercapto-ethyl)-quinazoline-2,4(1H,3H)-dione of Formula I, wherein $R^1$ and $R^2$ are both H, and n is 1, having a M.P. of 193° C.–195° C.

EXAMPLE 5

Preparation of
6-bromo-3-(2-mercaptoethyl)-quinazoline-2,4(1H,3H)-dione

This is a compound of Formula I, wherein $R^1$ is 6-Br, $R^2$ is H, and n is 1. The preparation of this compound is carried out in the same manner as in Example 4. M.P.: 298°–300° C., yield: 52% (based on the last step of the synthesis). The following intermediates were isolated and characterized:

(a) Bis-[2-(-amino-5-bromo-benzoylamino)-ethyl]-disulfan of Formula XIII, wherein $R^1$ is 5-Br, $R^2$ is H, and n is 1. Yield is 47% (after recrystallization from ethanol), and M.P. is 190° C.-195° C. (chloroform/n-hexane (1:1)).

(b) Bis[2-(6-bromo-2,4-dioxo-1,2,3,4-tetrahydro-quinazoline-3-yl]-ethyl]-disulfan of Formula XV, wherein $R^1$ is 6-Br, $R^2$ is H, n is 1. Yield of 60% (after recrystallizing from dimethylformamide), having a M.P. of 334° C.-336° C. (dimethylformamide).

EXAMPLE 6

3-(3-Mercapto-propyl)-quinazoline-2,4(1H,3H)-dione

This is a compound of Formula I, wherein $R^1$ and $R^2$ are both H, and n is 2. 24.5 g 2H-3,1-benzoxazine-2,4(1H)-dione of Formula III, wherein $R^1$ is H, is dissolved within 20 minutes in a solution of 12.3 g of 3-amino-1-propanol of Formula IV, wherein $R^2$ is H, and n is 2, and 45 ml water, with stirring, and is then heated for 10 minutes on a boiling water bath to obtain an initial solution.

Potassium hydroxide (17.0 g) is dissolved with heating in 225 ml ethanol. 36 ml carbon disulfide are added to the cooled solution. The reaction mixture is rested for 15 minutes in a closed vessel, then combined with the initial solution and refluxed for 3.5 hours under a hood. Then about 70 to 80 ml the solvent mixture is distilled off and the remaining reaction mixture is cooled and acidified with glacial acetic acid and rested for at least 3 hours to crystallize. 24.3 g TLC-pure 3-(3-hydroxy-propyl)-2-thioxo-2,3-dihydro-quinazoline-4(1H)-one is obtained of Formula VI, wherein $R^1$ and $R_2$ are both H, and n is 2, having a M.P. of 174° C.-176° C.

After the addition of about 200 ml water to the mother liquor, a further 4.0 g of almost TLC-pure crude product can be obtained. It is possible to recrystallize the compound from ethanol.

300 g of the dry, crude product obtained above is refluxed for 2.5 hours with 300 ml concentrated hydrochloric acid under a hood. The escaping HCl vapors have to be carefully disposed of. Then 2.7 l water is added to the reaction mixture and refluxing is continued for a further 20 hours. After cooling, the precipitate is filtered off with suction, and dried in air or in a drying oven at 30° C. to 40° C. The product is recrystallized from 1-propanol, with a yield of pure product of 83%, having a M.P. of 165° C.-167° C.

In a second process variant 30 g of 3-(3-hydroxy-propyl)-2-thioxo-2,3-dihydroquinazoline-4(1H)-one of Formula VI, wherein $R^1$ and $R^2$ are both H, and n is 2, is heated with a mixture of 30 ml glacial acetic acid and 12 ml concentrated sulfuric acid. After the addition of about 330 ml water, refluxing is continued for 15 hours. The product is worked up and purified as in the preceding process variant. The yield of almost TLC-pure crude product is 85%, with a M.P. of 165° C.-167° C. (1-propanol).

EXAMPLE 7

Preparation of
3-(2-mercapto-propyl)-quinazoline-2,4(1H,3H)-dione

This is a compound of Formula I, wherein $R^1$ is H. $R^2$ is a CH$_3$ derivative, and n is 1. 24.5 g 2H-3,1-Benzoxazine-2,4(1)-dione of Formula III, wherein $R^1$ is H, is reacted in a method similar to that of Example 6 with 12.3 g of 2-amino-1-propanol of Formula IV, wherein $R^2$ is CH$_3$, and n is 1, to form an initial solution.

The procedure of Example 6 is followed by using 17.0 g potassium hydroxide, 225 ml ethanol, and 36 ml carbon disulfide (the corresponding amount of potassium methyl xanthogenate can also be used). The product is combined with the initial solution, and is converted once more by the method of Example 6 to an almost TLC-pure 3-(2-hydroxypropyl)-2-thioxo-2,3-dihydro-quinazoline-4(1H)-one of Formula VI, wherein $R^1$ is H, $R^2$ is a CH$_3$ residue, and n is 1. Recrystallization from methanol is possible.

30 g of the dry crude product obtained above is converted by the same method of Example 6 to 3-(2-mercaptopropyl)-quinazoline-2,4(1H,3H)-dione of Formula I, wherein $R^1$ is H, $R^2$ is a CH$_3$ residue, and n is 1. The duration of the heating with concentrated hydrochloric acid is initially 2 hours, and after the addition of water, it is a further 15 hours. After recrystallization of the crude product from toluene, 22.4 g of pure product are obtained with a yield of 69% having M.P. of 206° C.-208° C.

EXAMPLE 8

Preparation of
6-chloro-3-(3-mercapto-propyl)-quinazoline-2,4(1H,3H)-dione

This is a compound of Formula I, wherein $R^1$ is 6-Cl, $R^2$ is H, and n is 2. The preparation is similar to that of Example 6, from 12.5 g 6-chloro-2H-3,1benzoxazine-2,4(1H)-dione, 5.8 g 3-aminopropanol, 40 ml water, 7.0 g potassium hydroxide, 100 ml ethanol, and 7.5 ml carbon disulfide. The reaction time is 4 to 4.5 hours. Some of the solvent mixture (35 to 40 ml) is distilled off and the reaction solution is filtered. The filtrate is acidified with acetic acid. 6 g of crude 6-chloro-3-(3-hydroxy-propyl)-2-thioxo-2,3-dihydro-quinazoline-4-(1H)-one of Formula VI, wherein $R^1$ is 6-Cl, $R^2$ is H, and n is 2, is obtained. After the addition of about 150 g of ice to the filtrate, a further 1.1 g of crude product are obtained. The crude product can be recrystallized from 1-propanol. M.P.: 255° C.-257° C.

3.0 g of the recrystallized pure product is converted as in Example 6 to the crude 6-chloro-3-(3-mercapto-propyl)-quinazoline-2,4(1H,3H)-dione of Formula I, wherein $R^1$ is 6-Cl, $R^2$ is H, and n is 2. After recrystallization from 1-propanol, 1.96 g of pure product is obtained in a 66% yield.

EXAMPLE 9

Preparation of
3-(2-mercapto-ethyl)-quinazoline-2,4(1H,3H)-dione

This is a compound of Formula I, wherein $R^1$ and $R^2$ are both H, and n is 1.

(a) 4.5 g (20 mmoles of 3-(2-chloroethyl)-2,4-dioxo-1,2,3,4-tetrahydroquinazoline of Formula XVI, wherein $R^1$ and $R^2$ are both H, n is 1, and Hal is Cl is refluxed for 45 minutes with 3.1 g (40 mmoles) powdered thiourea in 100 ml methyl glycol. The reaction mixture his rested for 12 hours at 4° C., the separated precipitate is washed with a little ice water and dried in air. TLC-pure S-[2-[2,4-dioxo-1,2,3,4-tetrahydro-quinazoline-3-yl)-ethyl]-isothiuronium chloride of Formula XVII, wherein $R^1$ and $R^2$ are both H, n is 1, and Hal is Cl is obtained in a yield of 5.1 g, corresponding to 85% of the theoretical yield with a M.P. of 259° C.-262° C. (after boiling out with absolute ethanol). The mobile phase used for thin-layer chromatography is toluene/acetone/methanol in a ration of 7:2:1.

(b) 2.84 g (10 mmoles) of the compound prepared in Example 9(a) is added under a blanket of nitrogen to 150 ml sodium hydroxide solution (0.25 moles/l) at a temperature of −5° C. to +5° C., and stirred until the reaction is complete in a maximum of 20 minutes, while $N_2$ gas is continuously passed through and checked with TLC, and the reaction mixture is maintained at −18° C. Then the reaction solution is filtered, acidified with about 45 ml hydrochloric acid and kept for about 6 to 10 hours at about 4° C. in a closed vessel. The 3-(2-mercapto-ethyl)-quinazoline-2,4(1H,3H)-dione precipitate is filtered off, washed with water and, after dried in air, recrystallized from glacial acetic acid. The M.P. was 192° C.–194° C. (1-propanol).

EXAMPLE 10

Preparation of 3-(3-mercapto-propyl)-quinazoline-2,4(1H,3H)-dione

This is a compound of Formula I, wherein $R^1$ and $R^2$ are both H, and n is 2.

(a) 0.48 g (2 mmoles) 3-(3-Chloropropyl)-2,4-dioxo-1,2,3,4-tetrahydro-quinazoline of Formula XVI, wherein $R^1$ and $R^2$ are both H, n is 2, and Hal is Cl, is refluxed for 3 hours with 0.31 g (4 mmoles) powdered thiourea. The precipitate, formed after the addition absolute diethyl ether, is washed with a small amount of ice water. After drying in air, 0.29 g of pure S-[3-(2,4-dioxo-1,2,3,4-tetrahydro-quinazoline-3-yl)-propyl]-isothiuronium chloride of Formula XVII, wherein $R^1$ and $R^2$ are both H, n is 2, and Hal is Cl, is obtained. the yield is 46%, and the M.P. is 224° C.–228° C. (after boiling out with absolute ethanol).

(b) 3-(3-Mercapto-propyl)-quinazoline-2,4(1H,3H)-dione is obtained from the compound produced by Example 10(a), by a reaction similar to that described in Example 9(b). M.P. is 165° C.–167° C. (1-propanol).

EXAMPLE 11

Preparation of 3-(2-mercapto-propyl)-quinazoline-2,4(1H,3H)-dione

This is a compound of Formula I, wherein $R^1$ is H, $R^2$ is a $CH_3$ residue, and n is 1.

(a) S-[2-(2,4-dioxo-1,2,3,4-tetrahydro-quinazoline-3-yl)-propyl]-isothiuronium chloride of formula XVII, wherein $R^1$ is H, $R^2$ is a $CH_3$ residue, n is 1, and Hal is Cl, is obtained by starting from 3-(2-chloropropyl)-2,4-dioxo-1,2,3,4-tetrahydro-quinazoline of Formula XVI, wherein $R^1$ is H, $R^2$ is a $CH_3$ residue, n is 1, and Hal is Cl, and using the method of Example 10(a) and refluxing for 75 minutes. The yield is 0.32 g (51% of the theoretical yield), having a M.P. of 225° C.–232° C. (after boiling out with absolute ethanol).

(b) 3-(2-Mercapto-propyl)-quinazoline-2,4(1H,3H)-dione is obtained from the compound of Example 11(a) by using a reaction similar to that described in Example 9(b). The M.P. is 206° C.–208° C. (toluene).

EXAMPLE 12

Preparation of 6-methyl-3-(3-mercapto-propyl)-quinazoline-2,4(1H,3H)-dione

This is a compound of Formula I, wherein $R^1$ is 6-$CH_3$, $R^2$ is H, and n is 2.

(a) The method employed is similar to that of Example 10(a) and starts with 0.506 g (2 mmoles) 6-methyl-3-(3-chloropropyl)-2,4-dioxo-1,2,3,4-tetrahydro-quinazoline of Formula (XVI), wherein $R^1$ is a $CH_3$ residue, $R^2$ is H, n is 2, and Hal is Cl, 0.17 g (2.2 mmoles) of powdered thiourea, and 4 ml methyl glycol. After 12 hours at −15° C., 0.25 g and, after the addition of absolute diethyl ether to the filtrate, a further 0.08 g of S-[3-(6-methyl-2,4-dioxo-1,2,3,4-tetrahydro-quinazoline-3-yl)-propyl]-isothiuronium chloride of Formula XVII, wherein $R^1$ is a $CH_3$ residue, $R^2$ is H, n is 2, and Hal is Cl, is obtained with a yield of 49%, and M.P. of 151° C.–153° C. (after boiling out with absolute ethanol).

The 6-methyl-3-(3-chloropropyl)-2,4-dioxo-1,2,3,4-tetrahydro/quinazoline, which was used as starting material, was prepared by reacting of 6-methyl-3-(3-hydroxypropyl)-2,4-dioxo-1,2,3,4-tetrahydro-quinazoline, having a M.P. of 196° C.197° C. (ethanol, crystalline conversion at 182° C.–184° C.), with thionyl chloride. The method is similar to that described by Grout and Partridge (J. Org. Chem. 1960, p. 3546). M.P.: 194° C.–196° C. (ethanol). Yield: 91%.

(b) 6-Methyl-3-(3-mercaptopropyl)-quinazoline-2,4(1H,3H)-dione is obtained from the compound prepared in Example 12(a), by a reaction similar to that described in Example 9(b), M.P.: 272° C.–274° C. (1-propanol).

EXAMPLE 13

Preparation of 6-chloro-3-(2-mercapto-ethyl)-quinazoline-2,4(1H,3H)-dione

This is a compound of Formula I, wherein $R^1$ is 6-Cl, $R^2$ is H, and n is 1. This compound is prepared by a method similar to that described in Examples 9 to 12. M.P. 331°–333° C. (glacial acetic acid).

EXAMPLE 14

The following compounds can be prepared by methods similar to those of Examples 1 to 13:

(a) 6-Methyl-3-(2-mercapto-ethyl)-quinazoline-2,4(1H,3H)-dione

M.P.: 309° C.–311° C. (1-propanol)

(b) 6-Bromo-3-(3-mercapto-propyl)-quinazoline-2,4(1H,3H)-dione

M.P.: 220° C.–221° C. (glacial acetic acid)

(c) 6-Fluoro-3-(2-mercapto-ethyl)-quinazoline-2,4(1H,3H)-dione

M.P.: 240° C.–242° C. (1-propanol)

(d) 6-Fluoro-3-(2-mercapto-propyl)-quinazoline-2,4(1H,3H)-dione

M.P.: 180° C.–181° C. (1-propanol)

(e) 6,7-Dimethoxy-3-(2-mercapto-propyl)-quinazoline-2,4(1H,3H)-dione

M.P.: 262° C.–264° C. (ethanol)

EXAMPLE 15

Tablets are prepared with 45.0 mg of 3-(2-mercapto-ethyl)-quinazoline-2,4(1H,3H)-dione as the active ingredient. In addition to the active ingredient, each tablet also contains 35.0 mg lactose, 25.0 mg potato starch, 3.5 mg polyvinylpyrrolidone, and 1.5 mg magnesium stearate.

The powdered active ingredient is mixed with potato starch and lactose. The mixture is uniformly wetted with a 20% ethanolic solution of the polyvinylpyrrolidone, passed through a 1.5 mm mesh screen, dried at 40° C., and then passed through a 1.0 mm mesh screen. The resulting granulate is mixed with magnesium stearate and pressed into tablets of 110 mg each.

EXAMPLE 16

Sugar-coated pill is prepared with 30.0 mg of 3-(2-mercapto-ethyl)-quinazoline-2,4(1H,3H)-dione as the active ingredient. The core of the sugar-coated pill contains in addition to the active ingredient, 30 mg lactose, 16.5 mg corn starch, 2.8 mg polyvinylpyrrolidone, and 0.7 mg magnesium stearate.

The powdered active ingredient is mixed with lactose and corn starch, and is then uniformly moistened with a 20% ethanolic solution of polyvinylpyrrolidone, then the mix is passed through a 1.5 mm mesh screen, dried at 40° C., and then passed R through a 1.0 mm mesh screen. The granulate obtained is mixed with magnesium stearate and pressed into tablet cores of 80 mg each, for sugar-coated pills in the customary manner. The cores, so prepared, are sugar coated and polished in the customary manner.

We claim:

1. A compound or its tautomer of Formula I,

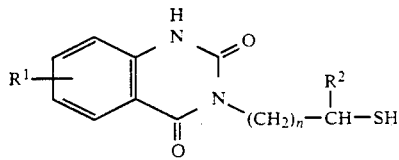

wherein
R$^1$ is hydrogen, a 6-methyl, 6-fluoro, 6-chloro, 6-bromo, or 6,7-dimethoxy residue,
R$^2$ is hydrogen, or a methyl residue,
and n is 1 or 2,
and tautomers and their pharmaceutically acceptable alkali, or ammonium salts.

2. A compound of claim 1, being one of the following compounds, or tautomers or their pharmaceutically acceptable alkali or ammonium salts thereof:
3-(2-mercapto-ethyl)-quinazoline-2,4(1H,3H)-dione,
3-(2-mercapto-propyl)-quinazoline-2,4(1H)-dione,
3-(3-mercapto-propyl)quinazoline-2,4(1H,3H)-dione,
3-(3-mercapto-prop-1-yl)-6,7-dimethoxy-quinazoline-2,4(1H,3H)-dione,
6-chloro-3-(2-mercapto-ethyl)-quinazoline-2,4(1H,3H)-dione,
6-chloro-3-(3-mercapto-propyl)-quinazoline-2,4(1H,3H)-dione,
6-bromo-3-(2-mercapto-ethyl)-quinazoline-2,4(1H,3H)-dione,
6-bromo-3(3-mercapto-propyl)-quinazoline-2,4(1H,3H)-dione,
6-fluoro-3-(2-mercapto-ethyl)-quinazoline-2,4(1H,3H)-dione,
6-fluoro-3-(2-mercapto-propyl)-quinazoline-2,4(1H,3H)-dione,
6-methyl-3-(2-mercapto-ethyl)-quinazoline-2,4(1H,3H)-dione,
6-methyl-3-(3-mercapto-propyl)-quinazoline-2,4(1H,3H)-dione, and
6-7-dimethoxy-3-((2-mercapto-propyl)-quinazoline-2,4(1H,3H)-dione.

3. A pharmaceutical composition comprising as active ingredient a compound of Formula (I) of claim 1, its tautomer, or a pharmaceutically acceptable alkali, or ammonium salt thereof, together with one or more pharmaceutically inert carrier and/or adjuvant.

4. The composition of claim 3, wherein said active ingredient is one of the following compounds, or tautomers, or a pharmaceutically acceptable alkali or ammonium salt thereof:
3-(2-mercapto-ethyl)-quinazoline-2,4(1H,3H)-dione,
3-(2-mercapto-propyl)-quinazoline-2,4(1H)-dione,
3-(3-mercapto-propyl)quinazoline-2,4(1H,3H)-dione,
3-(3-mercapto-prop-1-yl)-6,7-dimethoxy-quinazoline-2,4(1H,3H)-dione,
6-chloro-3-(2-mercapto-ethyl)-quinazoline-2,4(1H,3H)-dione,
6-chloro-3-(3-mercapto-propyl)-quinazoline-2,4(1H,3H)-dione,
6-bromo-3-(2-mercapto-ethyl)-quinazoline-2,4(1H,3H)-dione,
6-bromo-3(3-mercapto-propyl)-quinazoline-2,4(1H,3H)-dione,
6-fluoro-3-(2-mercapto-ethyl)-quinazoline-2,4(1H,3H)-dione,
6-fluoro-3-(2-mercapto-propyl)-quinazoline-2,4(1H,3H)-dione,
6-methyl-3-(2-mercapto-ethyl)-quinazoline-2,4(1H,3H)-dione,
6-methyl-3-(3-mercapto-propyl)-quinazoline-2,4(1H,3H)-dione, and
6-7-dimethoxy-3-((2-mercapto-propyl)-quinazoline-2,4(1H,3H)-dione.

5. The composition of claim 4, incorporated into a dosage form suitable for medicinal administration, said dosage form being a tablet, sugar-coated pill, capsule, suppository, solution, or ampule.

* * * * *